United States Patent [19]
Bauer et al.

[11] Patent Number: 5,969,190
[45] Date of Patent: Oct. 19, 1999

[54] CYCLOHEXANEDIOL DERIVATIVES

[75] Inventors: Franz Bauer, Reinach, Switzerland; Lawrence F. Courtney, Basking Ridge, N.J.

[73] Assignee: Hoffmann-La Roche Inc., Nutley, N.J.

[21] Appl. No.: 09/079,656

[22] Filed: May 15, 1998

[30] Foreign Application Priority Data

May 23, 1997 [EP] European Pat. Off. .............. 97108355

[51] Int. Cl.$^6$ .......................... A61K 31/045; C07C 35/14
[52] U.S. Cl. .......................... 568/400; 514/738; 568/828; 568/833; 568/834
[58] Field of Search ..................................... 514/724, 725, 514/729, 738; 568/822, 823, 828, 832, 833, 834

[56] References Cited

U.S. PATENT DOCUMENTS

| | | | |
|---|---|---|---|
| 5,225,579 | 7/1993 | Tahara | 552/653 |
| 5,486,636 | 1/1996 | DeLuca et al. | 556/443 |

FOREIGN PATENT DOCUMENTS

| | | |
|---|---|---|
| 0 387 077 | 9/1990 | European Pat. Off. . |
| WO 95/01960 | 1/1995 | WIPO . |
| WO 95/19963 | 7/1995 | WIPO . |
| WO 96/16035 | 5/1996 | WIPO . |

OTHER PUBLICATIONS

Zhao, et al., "New Discoveries in Vitamin D Related Compounds", Proceedings of the Ninth Workshop on Vitamin D, Orlando, Florida (USA), pp. 87–88 (1994).

Kutner, et al, "Synthesis of Retiferol $RAD_1$ and $RAD_2$, the Lead Representatives of a New Class of des–CD Analogs of Cholecalciferol", Bioorganic Chemistry, vol. 23, pp. 22–32 (1995).

Gilchrest, Retinoids and photodamage, British Journal of Dermatology, vol. 127, Suppl. 41, pp. 14–20, (1992).

Sicinski, et al., Synthesis and Biological Activity of $1\alpha,25$–Dihydroxy–18–norvitamin $D_3$ and $1\alpha,25$–Dihydroxy–18, 19–dinorvitamin $D_3$, J Med. Chem. vol. 39, pp. 4497–4506 (1996).

*Primary Examiner*—Howard C. Lee
*Attorney, Agent, or Firm*—George E. Johnston; William H. Epstein; Lewis J. Kreisler

[57] ABSTRACT

The compound, (E)-(1R,3R)-5-[(R)-11-hydroxy-7,11-dimethyl-dodec-2-enylidene]-cyclohexane-1,3-diol of the formula I:

is useful in the treatment or prevention of hyperproliferative skin diseases, particularly psoriasis, basal cell carcinomas, disorders of keratinization and keratosis; or for reversing the conditions associated with photodamage.

9 Claims, No Drawings

CYCLOHEXANEDIOL DERIVATIVES

SUMMARY OF THE INVENTION

The invention relates to the novel compound, (E)-(1R, 3R)-5-[(R)-11-hydroxy-7,11-dimethyl-dodec-2-enylidene]-cyclohexane-1,3-diol of the formula I:

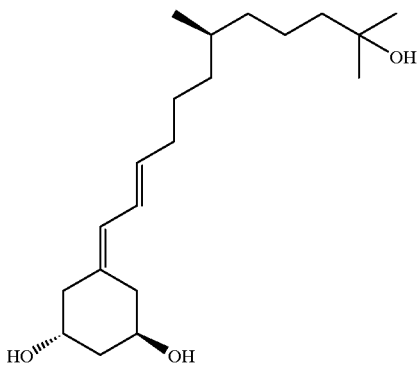

The compound of formula I (herein after the Compound) possesses the activity of inducing epidermal repair mechanisms, illustrated by causing an increase in epidermal proliferation in normal skin. As a result the Compound can also be utilized in reversing the conditions associated with photodamage, particularly for the oral or topical treatment of the skin damaged through sun exposure, the effects of wrinkling, elastosis and premature aging. Since an increase of epidermal proliferation in normal epidermis is indicative of a normalization of the epidermal proliferation in hyperproliferative disorders, the Compound of the invention can also be utilized to treat or prevent hyperproliferative skin diseases such as psoriasis, basal cell carcinomas, disorders of keratinization and keratosis; neoplastic diseases; disorders of the sebaceous glands such as acne and seborrhoic dermatitis.

The present invention furthermore relates to a process for the preparation of the Compound, pharmaceutical compositions containing the Compound, and the use of the Compound for the treatment and prevention of the above mentioned disorders, and for the manufacture of pharmaceutical compositions for the treatment and prevention of the above mentioned disorders.

DETAILED DESCRIPTION OF THE INVENTION

The Compound can be obtained by cleavage of the silyl protecting groups contained in a compound of formula II:

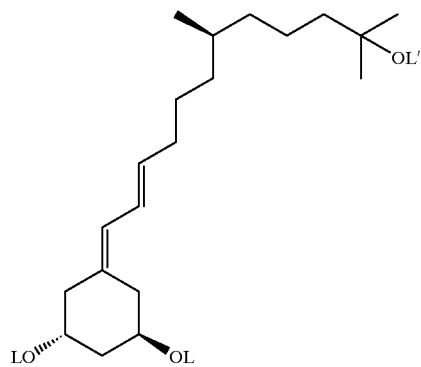

wherein L and L' are each independently a silyl protecting group. Any conventional silyl protecting group can be utilized. L is preferably tert-butyldimethyl-silyl (TBDMS) and L' preferably trimethyl-silyl [Si(Me)$_3$].

The cleavage can be effected by reacting the compound of formula I with a cleaving reagent in any conventional ether solvent. As used herein the term "ether" refers to an organic compound having an oxygen atom bonded to two carbon atoms with the general formula R-O-R'. Both linear and cyclic ethers (e.g. tetrahydrofuran) are included. The cleaving reagent is preferably tetrabutylammonium fluoride (TBAF; nBu$_4$NF) and the ether solvent is preferably tetrahydrofuran (THF). An excess of cleaving reagent is used, the ratio of the cleaving reagent to the compound of formula II preferably being at least about three equivalents to one at the start of the reaction, most preferably about five and one quarter equivalents to one. The reaction is preferably carried out at a temperature from about 30° C. to about 70° C. The reaction can be carried out under reflux, especially when the reaction temperature is close to or greater than the boiling point of the solvent. When the ether solvent is THF, the preferred reaction time is about 50° C. At a reaction temperature of about 50° C. a reaction time of about 2 hours is generally sufficient. At lower temperatures the reaction time will be longer. A higher temperature will generally allow a shorter reaction time, but may result in greater amounts of degradation products.

The intermediates II, which are novel and as such are a further object of the present invention, can be prepared in a manner known per se, e.g. as shown in the following reaction scheme, where L is TBDMS and L' is Si(Me)$_3$, and as described in detail in Example 1 hereinbelow.

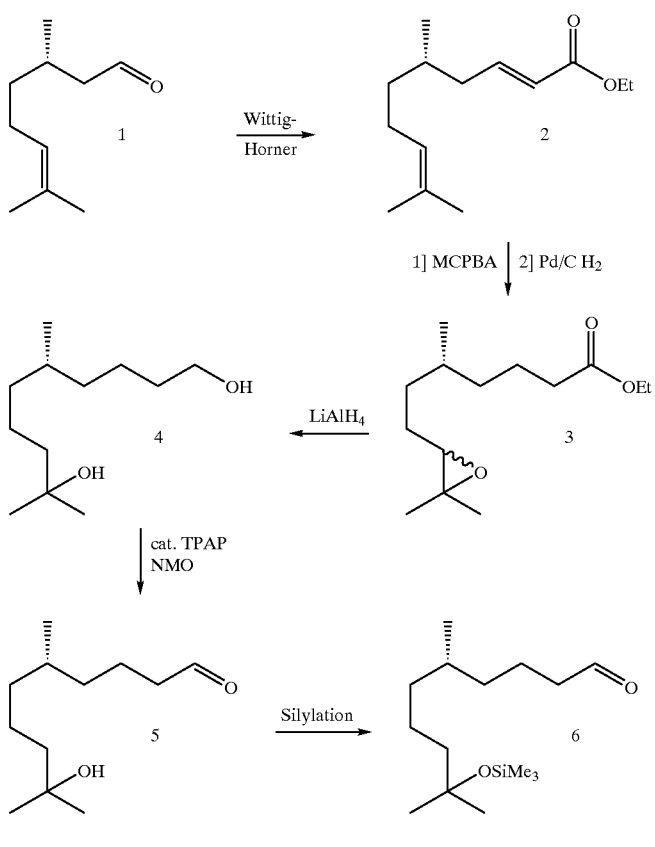

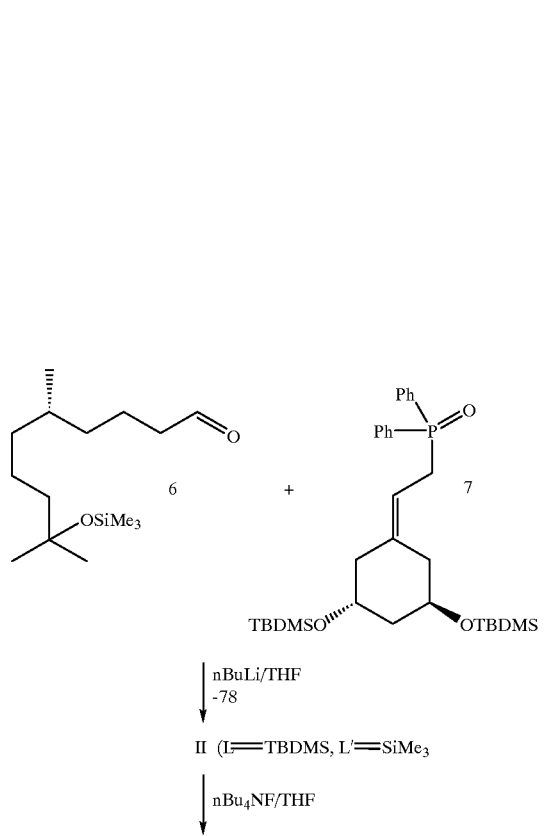

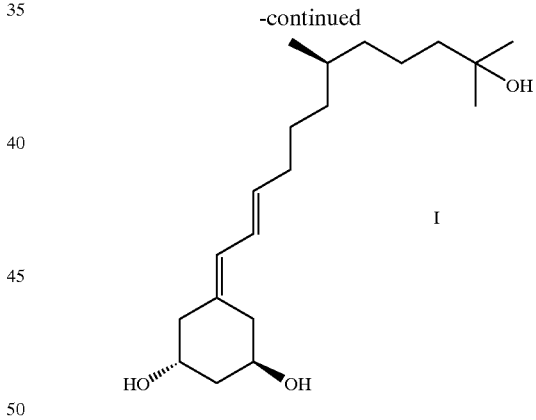

The Compound can be administered orally, for the treatment or prevention of hyperproliferative skin diseases such as psoriasis, basal cell carcinomas, disorders of keratinization, and keratosis, or for the treatment of neoplastic diseases, to warmblooded animals which need such treatment. More specifically, the Compound as described above can be administered orally to an adult human in dosages that are in the range of about 50 μg to 3 mg per day for the treatment of the above diseases.

The Compound can be administered topically, for the treatment or prevention of hyperproliferative skin diseases such as psoriasis, to warmblooded animals which need such treatment. More specifically, the Compound can be administered topically in dosages that are in the range of about 50 μg to 5 mg per gram of topical formulation, for the treatment of the above diseases.

The Compound can also be administered orally or topically for reversing the conditions associated with photodamage. More specifically, the Compound as described above can be administered orally to an adult human in dosages that are in the range of about 50 $\mu$g to 3 mg per day. The Compound can be administered topically in dosages that are in the range of about 50 $\mu$g to 5 mg per gram of topical formulation.

The dosage of the Compound can vary within wide limits depending on the illness to be treated, the age and the individual condition of the patient and on the mode of administration and will, of course, be fitted to the individual requirements in each particular case.

In accordance with this invention, a pharmaceutical Composition contains an effective amount of the Compound and a pharmaceutically acceptable carrier. For oral administration, an effective amount is from 50 $\mu$g to 3 mg, more specifically 0.1 mg to 1 mg, and still more specifically about 0.5 mg. For topical administration, an effective amount is from 50 $\mu$g to 5 mg per gram of topical formulation, more specifically 0.5 mg to 5 mg, and still more specifically about 1 mg.

Oral dosage forms comprising the Compound, may be incorporated in capsules, tablets and the like with pharmaceutically acceptable carrier materials. Illustrative of such carrier materials which may be incorporated into capsules, and the like are the following: an antioxidant such as butylated hydroxytoluene (BHT), butylated hydroxyanisole (BHA) or alpha-tocopherol; an emulsifier such as polyethylene glycol; a solubilizer such as a short chain or middle chain triglyceride, e.g. a caprylic/capric triglyceride such as MIGLYOL or NEOBEE; a binder such as gum tragacanth, acacia, corn starch, or gelatin; an excipient such as dicalcium phosphate; a disintegrating agent such as corn starch, potato starch or algenic acid; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

In accordance with this invention an oral dosage form can be encapsulated in a gelatin capsule, wherein the oral dosage form comprises from 50 $\mu$g to 3 mg, more specifically from 0.5 mg to 3 mg, still more specifically about 1 mg, of (E)-(1R,3R)-5-[(R)-11-hydroxy-7,11-dimethyl-dodec-2-enylidene]-cyclohexane-1,3-diol; about 0.016 mg butylated hydroxytoluene; about 0.016 mg butylated hydroxyanisole; and q.s. (up to about 160 mg) of a middle chain triglyceride oily vehicle. Suitable middle chain triglycerides include caprylic/capric triglyceride derived from fractionated coconut oil (e.g. NEOBEE M-5) and other caprylic/capric triglycerides (e.g. MIGLYOL 812).

In accordance with this invention an oral dosage form can be encapsulated in a gelatin capsule, in which the oral dosage form comprises from 50 $\mu$g to 3 mg, more specifically from 0.5 mg to 3 mg, still more specifically about 1 mg, (E)-(1R,3R)-5-[(R)-11-hydroxy-7,11-dimethyl-dodec-2-enylidene]-cyclohexane-1,3-diol; about 0.016 mg alpha-tocopherol; and q.s. (up to about 160 mg) of a middle chain triglyceride oily vehicle. For example, the middle chain triglyceride can be a caprylic/capric triglyceride (e.g. MIGLYOL 812).

Topical dosage forms comprising the Compound include: ointments and creams encompassing formulations having oleaginous, absorbable, water-soluble and emulsion-type bases such as petrolatum, lanolin, polyethylene glycols and the like. Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like. Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine. Other carriers which may be suitably employed in topical dosage forms include a thickening/suspending agent such as cetyl alcohol or stearyl alcohol; a surfactant such as sorbitan monostearate (e.g. SPAN 60), glyceryl monostearate and polyoxyethylene glycol stearate blend (e.g. ARLACEL 165) or polysorbate 60 (e.g. TWEEN 60); a liquid oily phase such as mineral oil, a cosolvent such as propylene glycol, a preservative such as propylparaben or methylparaben; an antioxidant such as BHT or BHA; a sweetening agent such as sorbitol; a chelating agent such as edetate disodium; and a liquid aqueous phase such as distilled water.

As used herein, the term "topical" denotes the use of the active ingredient, incorporated in a suitable pharmaceutical carrier, and applied at the site of the disorder for the exertion of local action. Accordingly, the topical composition include those pharmaceutical forms in which the Compound is applied externally by direct contact with the skin. The topical dosage forms comprise gels, creams, lotions, ointments, powders, aerosols and other conventional forms for applying medication to the skin obtained by admixing the Compound with known pharmaceutical topical carrier materials.

In an embodiment, this invention provides a pharmaceutical composition suitable for topical administration which comprises, per gram of the composition: from 50 $\mu$g to 5 mg, more specifically from 0.5 mg to 5 mg, still more specifically about 1mg of (E)-(1R,3R)-5-[(R)-11-hydroxy-7,11-dimethyl-dodec-2-enylidene]-cyclohexane-1,3-diol; about 1.5 mg cetyl alcohol; about 2.5 mg stearyl alcohol; about 2.0 mg sorbitan monostearate (e.g. SPAN 60); about 4.0 mg glyceryl monstearate and polyoxyethylene glycol stearate blend (e.g. ARLACEL 165); about 1.0 mg polysorbate 60 (e.g. TWEEN 60); about 4.0 mg mineral oil; about 5.0 mg propylene glycol; about 0.05 mg propylparaben; about 0.05 mg butylated hydroxyanisole; about 2.0 mg sorbitol solution; about 0.01 edetate disodium; about 0.018 mg methylparaben; and distilled water q.s.

This invention will be better understood by reference to the following examples, which are illustrative only and are not intended to limit the invention which is defined in the claims.

Example 1—Synthesis (E)-(1R,3R)-5-[(R)-11-Hydroxy-7,11-dimethyl-dodec-2-enylidene]-cyclohexane-1,3-diol was prepared as follows:

A) 8.55 g of carefully dried (3R,5R)-[2-[3,5-bis-(t-butyldimethyl-silanyloxy)-cyclohexylidene]-ethyl]-diphenyl-phosphine oxide (*Tetrahedron Lett*. 32, 7663 (1991)) was dissolved in 90 ml of abs. THF and treated at −78° with 10.9 ml of nBuLi (1.6M, hexane). After 20 minutes, 2.27 g of (S)-5,9-dimethyl-9-trimethylsilanyloxy-decanal, dissolved in a small amount of THF, was added dropwise to the deep red solution. The mixture was kept for 0.5 h at −78° and for 4 h at ambient temperature. After quenching with crushed ice/ $KH_2PO_4$, the product was extracted twice with ether, washed with water and brine, dried over sodium sulfate and the solvents removed i.V. Flash chromatography ($SiO_2$, hexane/ AcOEt) yielded in the less polar fractions 3.840 g of (R)-1-[(3R,5R)-3,5-bis-(tert-butyldimethyl-silanyloxy)-cyclohexylidene]-7,11-dimethyl-11-trimethylsilanyloxy-dodec-2-ene, as colorless oil, which was deprotected as described in the following paragraph. 2.40 g of phosphine oxide, which had been used in excess, were recovered in the more polar fractions.

B) 4.88 g of the silylated diene, prepared as described above, were treated with 5.25 equivalents of anhydr. TBAF (0.5M inTHF) at 50° for 2 h. The reaction mixture was poured onto crushed ice, extracted twice with AcOEt, washed with water and brine, dried over sodium sulfate and evaporated to dryness. Flash chromatography ($SiO_2$, hexane/AcOEt=1/2) yielded 2.304 g of the title compound as colorless oil, contaminated with roughly 10% of the Z-isomer.

MS: $(M-H_2O)^+$306, $(M-2H_2O)^+$288; NMR: (1H, DMSO, δ, TMS) 0.83 (d, 3H), 1.05 (s, 6H), 1.05–1.43 (m, 17H), 1.62 (t, 2H), 1.9–2.15 (m, 4H), 2.23 (dd, 1H), 2.36 (dd, 1H), 3.83 (m, 2H), 4.04 (s, 1H, OH), 4.42 (d, 1H, OH), 4.45 (d, 1H, OH), 5.54 (dt, 1H), 5.75 (d, 1H), 6.24 (dd, 1H); IR (cm⁻): 3369, 2929, 1461, 1377, 1216, 1049, 963.

The starting decanal derivative was prepared as follows:

a) 16.05 g of triethyl phosphonoacetate was dissolved in 160 ml of abs. THF and treated at 0° with 8.32 g of KOtBu. After 1 h at that temperature, 8.16 g of (−)-citronellal, dissolved in 30 ml of abs. THF, was added to the white suspension. 1.5 h later, the reaction was quenched by pouring onto crashed ice/$NH_4Cl$, extracted twice with ether, washed with water and brine, dried over sodium sulfate and evaporated to dryness. Flash chromatography ($SiO_2$, hexane/AcOEt=97/3) produced 8.84 g of (E)-(S)-5,9-dimethyl-deca-2,8-dienoic acid ethyl ester as colorless oil.

b) 13.54 g of 3-chloro-perbenzoic acid (MCPBA, 70%) was dissolved in 30 ml of $CH_2Cl_2$ and cooled to 0°. 8.84 g of (E)-(S)-5,9-dimethyl-deca-2,8-dienoic acid ethyl ester dissolved in 15 ml of $CH_2Cl_2$, was slowly added and the mixture kept for an additional 0.5 h in the ice bath. The reaction was then quenched by pouring onto crushed ice/sodium pyrosulfite, extracted twice with AcOEt, washed with 2N NaOH, water and brine, dried over sodium sulfate and evaporated to dryness to yield 9.59 g of (5R)-7-((RS)-3,3-dimethyl-oxiranyl)-5-methyl-hept-2-enoic acid ethyl ester as 1/1 epimeric mixture, sufficiently pure for the next step.

c) 9.59 g of (5S)-7-((RS)-3,3-dimethyl-oxiranyl)-5-methyl-hept-2-enoic acid ethyl ester was hydrogenated at RT in 57 ml of AcOEt over 960 mg of Pd/C (5%) for 6 h. At that time, GC analysis indicated the complete disappearance of starting material. Filtration and flash chromatography ($SiO_2$, hexane/AcOEt=9/1) afforded 7.98 g of (5R)-7-((RS)-3,3-dimethyl-oxiranyl)-5-methyl-heptanoic acid ethyl ester (roughly 1/1 epimeric mixture) as colorless oil.

d) 7.98 g of (5R)-7-((RS)-3,3-dimethyl-oxiranyl)-5-methyl-heptanoic acid ethyl ester was dissolved in 130 ml of abs. THF and treated carefully at −25° with 2.49 g of $LiAlH_4$. The reaction mixture was kept for 0.5 h at −20° and for 5 h at ambient temperature. The excess of reagent was destroyed by successively adding AcOEt and MeOH. 3N aq. NaOH was then added in order to hydrolyse the aluminum alkoxides, but in such small quantities that the formation of a second aq. layer was avoided. Filtration over sodium sulfate, washing with ether, and evaporation to dryness yielded a crude product which was purified by flash chromatography ($SiO_2$, hexane/AcOEt=1/1) to deliver 4.59 g of (R)-5,9-dimethyl-decane-1,9-diol as colorless oil, 96% pure according to GC.

e) 5.68 g of 4-methylmorpholine N-oxide (monohydrate) (NMO) and 31.5 g of molecular sieves (powder, 4A) in 200 ml of abs. $CH_2Cl_2$ were stirred for 0.25 h at ambient temperature. 500 mg of tetrapropylammonium perrhutenate (TPAP) was added, before a solution of 4.59 g of (R)-5,9-dimethyl-decane-1,9-diol in 20 ml of abs. $CH_2Cl_2$ was added within 1 h. 15 minutes later, the reaction mixture was filtered and the solvents removed i.V. Flash chromatography ($SiO_2$, hexane/AcOEt=7/3) afforded 3.103 g of (S)-9-hydroxy-5,9-dimethyl-decanal as colorless oil, 98.7% pure according to GC.

f) 3.10 g of (S)-9-hydroxy-5,9-dimethyl-decanal was dissolved in 60 ml of abs. $CH_2Cl_2$ and treated successively at 0° with 57 mg of DMAP, 7.0 ml of $NEt_3$ and 3.1 ml of TMS-Cl. The reaction mixture was kept for 30 minutes at RT and then poured onto crushed ice, extracted twice with ether, washed twice with water and brine, dried over sodium sulfate and evaporated to dryness. Flash chromatography ($SiO_2$, hexane/AcOEt= 95/5) yielded 3.90 g of (S)-5,9-dimethyl-9-trimethylsilanyloxy-decanal as colorless oil, 98.6% pure according to GC.

Example 2—In Vivo Activity

Pharmaceutical properties of the Compound were determined according to the following procedure:

The Compound was orally applied to Göttingen minipigs at different doses for seven days. The pigs were daily observed as to adverse effects (behavior, mobility, stool). At day seven bromodeoxyuridine (4 mg/kg) was injected intravenously in the treated pigs and one hour later skin biopsies (6 mm diameter) and blood were taken from the animals for analysis. The skin biopsies were fixed in formalin, and paraffin sections were prepared using standard procedures. Using standard immuno-histochemical techniques, cells in the S-phase (DNA synthesis phase) were labelled by binding of a specific monoclonal antibody against the thymidine analogue, bromodeoxyuridine. The number of labelled epidermal cells per unit of length along the surface was taken as a measure of epidermal proliferative activity.

Results

The Compound was extremely well tolerated and caused an increase in epidermal proliferation in a large dose range (100–4000 μg/kg) without any adverse effect (neither visible nor with regard to clinical chemical parameters). The bromodeoxyuridine technique for kinetic studies of human epidermis is further discussed in Rijzewijk et al. Epithelia (1987) 1, 323–333.

Conclusion

Enhancement of epidermal proliferation is indicative of epidermal repair mechanisms, e.g. in photodamage. Furthermore, an increase of epidermal proliferation in vivo in normal epidermis is indicative of a normalization of the epidermal proliferation in hyperproliferative disorders, as is known for instance for retinoids.

The following pharmaceutical compositions are prepared:

Example 3

| Soft Gelatin Capsule | mg/Capsule |
| --- | --- |
| Compound | 0.5 |
| Butylated Hydroxytoluene (BHT) | 0.016 |
| Butylated Hydroxyanisole (BHA) | 0.016 |
| Fractionated Coconut Oil (NEOBEE M-5) or MIGLYOL 812 | q.s. up to 160.0 |

Example 4

| Soft Gelatin Capsule | mg/Capsule |
| --- | --- |
| Compound | 0.5 |
| α-Tocopherol | 0.016 |
| MIGLYOL 812 | q.s. up to 160.0 |

Example 5

| Topical Cream | mg/g |
| --- | --- |
| Compound | 0.5 |
| Cetyl Alcohol | 1.5 |
| Stearyl Alcohol | 2.5 |
| SPAN 60 (Sorbitan monostearate) | 2.0 |
| ARLACEL 165 (Glyceryl monostearate and polyoxyethylene glycol stearate blend) | 4.0 |
| TWEEN 60 (polysorbate 60) | 1.0 |
| Mineral Oil | 4.0 |
| Propylene Glycol | 5.0 |
| Propylparaben | 0.05 |
| BHA | 0.05 |
| Sorbitol Solution | 2.0 |
| Edetate Disodium | 0.01 |
| Methylparaben | 0.18 |
| Distilled Water | q.s. |

What is claimed is:

1. The compound, (E)-(1R,3R)-5-[(R)-11-hydroxy-7,11-dimethyl-dodec-2-enylidene]-cyclohexane-1,3-diol.

2. A compound of formula:

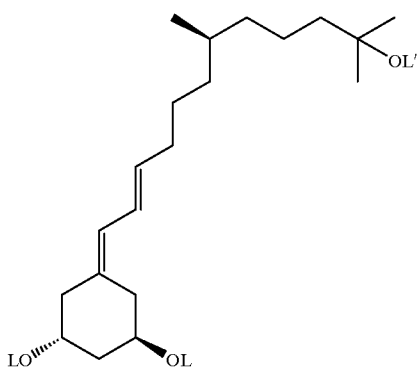

II wherein each L is tert-butylmethyl-silyl and L' is trimethyl-silyl.

3. A process for producing (E)-(1R,3R)-5-[(R)-11-hydroxy-7,11-dimethyl-dodec-2-enylidene]-cyclohexane-1,3-diol, comprising reacting a compound of formula

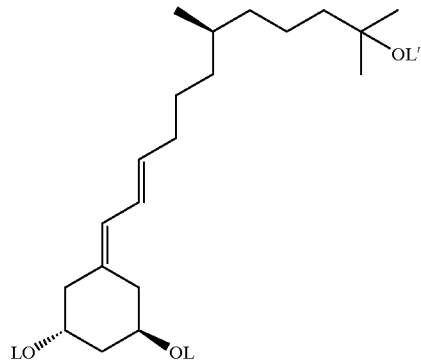

II wherein L is tert-butylmethyl-silyl and L' is trimethyl-silyl, with tetrabutylammonium fluoride in an ether solvent, wherein the ratio of the tetrabutylammonium fluoride to the compound of formula II at the start of the reaction is at least about three equivalents to one, thereby producing the (E)-(1R,3R)-5-[(R)-11-hydroxy-7,11-dimethyl-dodec-2-enylidene]-cyclohexane-1,3-diol.

4. The process of claim 3, wherein the ether solvent is tetrahydrofuran.

5. The process of claim 4, wherein the reaction is carried out at a temperature from about 30° C. to about 70° C.

6. The process of claim 4, wherein the the ether solvent is tetrahydrofuran and the reaction is carried out at a temperature of about 50° C.

7. An oral dosage form encapsulated in a gelatin capsule, wherein the oral dosage form comprises from 0.1 mg to 1 mg (E)-(1R,3R)-5-[(R)-11-hydroxy-7,11-dimethyl-dodec-2-enylidene]-cyclohexane-1,3-diol; about 0.016 mg butylated hydroxytoluene; about 0.016 mg butylated hydroxyanisole; and about 160 mg of a caprylic/capric triglyceride.

8. An oral dosage form encapsulated in a gelatin capsule, wherein the oral dosage form comprises from 0.1 mg to 1 mg (E)-(1R,3R)-5-[(R)-11-hydroxy-7,11-dimethyl-dodec-2-enylidene]-cyclohexane-1,3-diol; about 0.016 mg alpha-tocopherol; and about 160 mg of a caprylic/capric triglyceride.

9. A pharmaceutical composition comprising, per gram of the composition:

from 0.1 mg to 1 mg (E)-(1R,3R)-5-[(R)-11-hydroxy-7,11-dimethyl-dodec-2-enylidene]-cyclohexane-1,3-diol;
about 1.5 mg cetyl alcohol;
about 2.5 mg stearyl alcohol;
about 2.0 mg sorbitan monostearate;
about 4.0 mg glyceryl monstearate and polyoxyethylene glycol stearate blend;
about 1.0 mg polysorbate 60;
about 4.0 mg mineral oil;
about 5.0 mg propylene glycol;
about 0.05 mg propylparaben;
about 0.05 mg butylated hydroxyanisole;
about 2.0 mg sorbitol solution;
about 0.01 edetate disodium;
about 0.018 mg methylparaben; and
distilled water q.s.

* * * * *